US00PP29584P2

(12) United States Plant Patent
O'Connell

(10) Patent No.: US PP29,584 P2
(45) Date of Patent: Aug. 7, 2018

(54) ***ECHEVERIA* 'ARCTIC ICE'**

(50) Latin Name: *Echeveria hybrida*
Varietal Denomination: Arctic Ice

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/731,160

(22) Filed: Apr. 26, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct *Echeveria* cultivar named 'Arctic Ice' is disclosed, rapid, robust growth and improved resistance to *Fusarium echeveriae*. Plants are distinctively compact and mounding with attractive uniform rosettes. Foliage has an opalescent quality. *Echeveria* is a popular genus, typically produced as container plants for the patio or as landscape plants. The new variety is also suitable for florist purposes.

2 Drawing Sheets

Latin name of the genus and species: *Echeveria hybrida*.
Variety denomination: 'ARCTIC ICE'.

BACKGROUND OF THE INVENTION

The new cultivar, *Echeveria* 'Arctic Ice', is the product of a planned breeding program. The new variety originated from a cross pollination of the proprietary, unpatented, seed parent, *Echeveria* 'E1 IV' with the pollen parent an unpatented, proprietary variety of *Echeveria* referred to as 'Lila's Surprise'. The cross pollination was made during February 2012 in Vista, Calif., at a commercial greenhouse. The new cultivar 'Arctic Ice' was selected by the inventor, Renee O' Connell, in March 2013, in Vista, Calif. at a commercial greenhouse.

Asexual reproduction of the new cultivar 'Arctic Ice' was first performed in Vista, Calif., at a commercial greenhouse, by terminal vegetative cuttings in September 2013. *Echeveria* 'Arctic Ice' has since produced at least 8 generations and has shown that the unique features of this cultivar are stable and reproduced true to type.

SUMMARY OF THE INVENTION

The cultivar 'Arctic Ice' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ARCTIC ICE'. These characteristics in combination distinguish 'ARCTIC ICE' as a new and distinct *Echeveria* cultivar:

1. *Echeveria* 'Arctic Ice' somewhat resembles *Echeveria elegans*, but is much more resistant to *Fusarium echeveriae* than is *Echeveria elegans*, and therefore can be used as a replacement for *Echeveria elegans* where a stronger plant is needed.

2. *Echeverias* are becoming very popular for use in decorative arrangements, including wedding bouquets. *Echeveria* hybrid 'Arctic Ice', displays an uncommon opalescent appearance to rosette, providing a beautiful addition to the palette available for succulent wedding bouquets.
3. *Echeveria* 'Arctic Ice' produces a more rounded "snowball" rosette than many other comparable white *Echeverias.*
4. *Echeveria* 'Arctic Ice', due to its more rapid and robust growth, provides enhanced production times in a commercial nursery, as compared with most other white *Echeverias.*
5. *Echeveria* 'Arctic Ice', with it robust growth, better resistance to *Fusarium echeveriae*, and compact, opalescent white rosette, is an excellent choice for use in a dish garden or as a potted plant on the patio.

PARENTAL COMPARISON

Plants of the new cultivar 'Arctic Ice' are similar to plants of the seed parent in most horticultural characteristics. However, plants of the new cultivar 'Arctic Ice' differ in the following:

1. *Echeveria* 'Arctic Frost' produces concentric rosettes of opalescent white, whereas *Echeveria* 'E1 IV' produces pale aqua rosettes.
2. *Echeveria* 'Arctic Frost' produces flowers that are slightly larger than those of *Echeveria* 'E1 IV'.
3. *Echeveria* 'Arctic Frost' is faster growing than *Echeveria* 'E1 IV'.
4. *Echeveria* 'E1 IV' produces more offsets than *Echeveria* 'Arctic Frost'.

Plants of the new cultivar 'Arctic Ice' are similar to the pollen parent in most horticultural characteristics. However, plants of the new cultivar 'Arctic Ice' differ in the following:

1. *Echeveria* 'Arctic Frost' produces rosettes of opalescent white, whereas the rosettes of *Echeveria* 'Lila's Surprise' are a powdery, matte white, with a tinge of blue.

2. The flowers of *Echeveria* 'Arctic Frost' are more fully tubular, whereas the flowers of *Echeveria* 'Lila's Surprise' tend to open more at the apical tips of the corolla.
3. The leaves of *Echeveria* 'Arctic Frost' are more obovate than those of *Echeveria* 'Lila's Surprise, which has spatulate leaves with obtuse apices.
4. *Echeveria* 'Arctic Frost' produces a more "snowball" rosette, whereas the rosette of *Echeveria* 'Lila's Surprise' is more flattened.
5. The leaves of *Echeveria* 'Arctic Frost' are thicker and more fleshy than those of *Echeveria* 'Lila's Surprise'.

COMMERCIAL COMPARISON

The new cultivar 'Arctic Ice' can be compared to the unpatented commercial variety *Echeveria* 'Perle van Nurnburg'. Plants of the new cultivar 'Arctic Ice' differ in the following:

1. *Echeveria* 'Arctic Frost' forms rounded rosettes of opalescent white, whereas *Echeveria* 'Perle von Nurnberg' forms rosettes of lavender.
2. *Echeveria* 'Arctic Frost' is more resistant to *Rhizoctonia solani* than is *Echeveria* 'Perle von Nurnberg'.
3. *Echeveria* 'Arctic Frost produces chunky, fleshy leaves, whereas *Echeveria* 'Perle von Nurnberg' produces thinner leaves, and for that reason, *Echeveria* 'Perle von Nurnberg' shows effects of drought, whereas the effects of drought are less discernible with *Echeveria* 'Arctic Frost'.
4. *Echeveria* 'Perle von Nurnberg', begins to grow taller with time, whereas *Echeveria* 'Arctic Frost' maintains a nearly acaulescent morphology.

The new cultivar 'Arctic Ice' can be compared to the unpatented, unnamed *Echeveria elegans*. Plants of the new cultivar 'Arctic Ice' are similar to *Echeveria elegans*. in most horticultural characteristics. However, plants of the new cultivar 'Arctic Ice' differ in the following:

1. *Echeveria* 'Arctic Ice' forms rosettes of frosty white, whereas *Echeveria elegans* forms rosettes of silver blue.
2. *Echeveria* 'Arctic Ice' is much more resistant to disease pressure, particularly *Fusarium echeveriae* than is *Echeveria elegans*.
3. *Echeveria* 'Arctic Ice' is faster growing and more robust growing than *Echeveria elegans*.
4. *Echeveria elegans* is more suited to climates where the summers are mild, whereas *Echeveria* 'Arctic Frost' is able to grow successfully where the summer temperatures are routinely 80 to 95 degree F.

BRIEF DESCRIPTION OF THE PHOTOGRAPHS

The accompanying photographs in FIG. 1 and FIG. 2 illustrate in full color typical plants of 'ARCTIC ICE' grown in a greenhouse in Vista, Calif. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Echeveria* plant. The following photographs depict plants grown under two different natural light conditions. Temperatures ranged from approximately 2° C. to 38° C. night and day. No artificial light, photoperiodic treatments or chemical treatments were given to the plants.

DETAILED BOTANICAL DESCRIPTION

Figure 1:
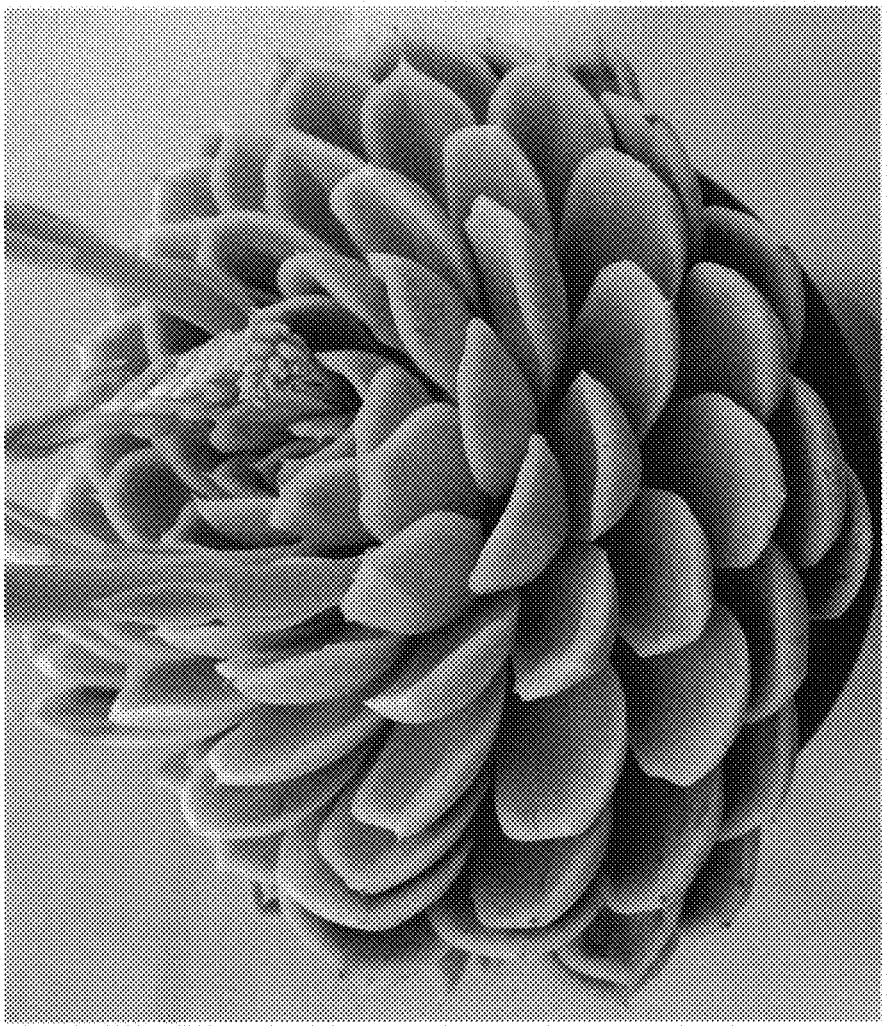
FIG. 1 illustrates in full color a typical of plant of *Echeveria* 'Arctic Ice' grown in a greenhouse in Vista, Calif. under moderate light conditions of approximately 2500 to 3500 foot candles. This figure highlight the foliar rosette.
Figure 2:
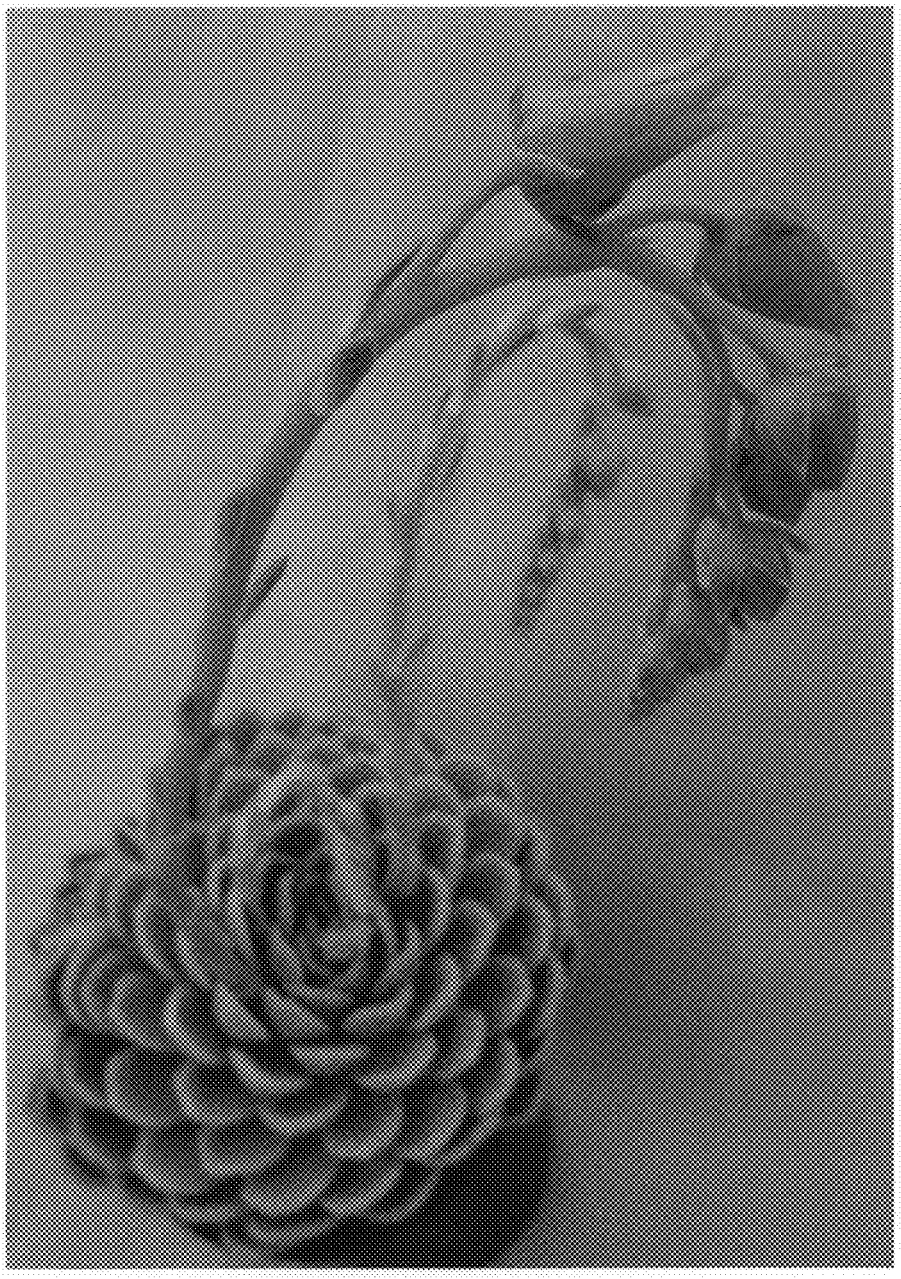
FIG. 2 illustrates in full color typical of plant of *Echeveria* 'Arctic Ice' with a flowering stem.

In the following description, color references are made to The Royal Horticultural Society Colour Chart, 2007, except where general terms of ordinary dictionary significance are used. The following observations and measurements describe 'Arctic Ice' plants in a commercial greenhouse in Vista, Calif. Temperatures ranged from 2° C. to 38° C. night and day. No artificial light, photoperiodic treatments or chemical treatments were given to the plants. Natural light conditions were approximately 2500 to 2500 fc of light. Measurements and numerical values represent averages of typical plant types.

Botanical classification: *Echeveria hybrida* 'ARCTIC ICE'.

PROPAGATION

Type of propagation typically used: Terminal vegetative cuttings, from side shoots.

Time to initiate roots: About 11 days at approximately 24° C.

Root description: Fibrous.

PLANT

Age of plant described: Approximately 4 months from a cutting.

Container size of the plant described: 4 inch.

Growth habit: Densely and somewhat flattened rosulette plant.

Height: Approximately 5 cm to top of highest leaf. Approximately 30 cm to top of highest inflorescence.

Plant spread: Approximately 15.0 cm.

Growth rate: Rapid.

Branching characteristics: Not typically observed. Moderate side rosette formation.

FOLIAGE

Leaf:

*Arrangement*.—Rosulate.

*Average length*.—Average range 4.0 to 5.5 cm.

*Average width*.—2.0 cm.

*Width at base*.—Average 1.5 cm.

*Thickness of leaf*.—Thickest section, near center of leaf 1.0 cm.

*Shape of blade*.—Spatulate, upper section angular.

*Apex*.—Truncate, to tapered truncate with a single, sharp mucronate tip, approximately 3 mm long.

*Base*.—Truncate.

*Margin*.—Entire.

*Attachment*.—Sessile.

*Texture of top surface*.—Glabrous. Glaucous.

*Texture of bottom surface*.—Glabrous. Glaucous.

*Appearance of top surface*.—Matte.

*Appearance of bottom surface*.—Matte.

*Quantity of leaves per rosette*.—Average range 80 to 100.

*Color*.—Young foliage upper side: Near RHS Greyed-Green 188A, margin near White 155D. When glaucous covering rubbed off main leaf blade color is Green 138A. Young foliage, under side: Near RHS Greyed-Green 188A, margin near White 155D. apical flush near Greyed-Purple N187B. When glaucous covering rubbed off main leaf blade color is Green 138A. Mature foliage upper side: Near RHS Greyed-Green 188A, margin near White 155D. When glaucous covering rubbed off main leaf blade color is Green 138A. Mature foliage, under side: Near RHS Greyed-Green 188A, margin near White 155D. When glaucous covering rubbed off main leaf blade color is Green 138A. Venation: There is no visual appearance of venation.

FLOWER

Natural flowering season: Irregularly occurring Spring through Summer.

Inflorescence type and habit: Long, erect, simple cincinnus typically with 10 to 15 flowers. 3 to 5 inflorescence per plant, depending on maturity and environmental conditions. Individual flowers semi-fleshy, campanulate.

Rate of flower opening: About 12 days from bud stage to open flower.

Flower longevity on plant: 2 to 4 weeks, depending upon ambient temperatures.

Total inflorescence size:

*Height*.—Approximately 5 to 12 cm, excluding peduncle.

*Width*.—Approximately 4.0 cm.

Corolla:

*Arrangement*.—Pentagonal, fused.

*Size*.—Length: Approximately 1.7 cm. Width: Approximately 1.1 cm at widest point. Lobe Length: Approximately 0.7 cm. Lobe width: Approximately 0.3 cm.

*Petals*.—Margin: Entire. Shape: Unfused section deltate. Apex: Acute. Base: Fused, approximately 90 percent of length. Texture: Glabrous.

Color:

*When opening*.—Petal color, outer surface: Bottom ⅓ near Greyed-Red 182D, mid section Orange-Red 32C, apex near Yellow 12C. Slightly glaucous when immature, glaucous coloration near Greyed-Purple N187C. Inner petals: Not visible until fully opened.

*Fully opened*.—Outer surface: Bottom ⅓ near Red 39A, with slightly glaucous coloration Greyed-Red 182D. Mid section Orange-Red 32D, apex near Yellow 13B. Inner surface: Near Yellow 13A, base Yellow-White 158D. Color Changes when Aging: Outer surface turns near Greyed-Purple 185C. Inner surface near Red 42C.

Bud: (near opening):

*Shape*.—Conical.

*Length*.—Approximately 1.1 cm.

*Diameter*.—Approximately 0.6 cm.

*Color*.—Near Red 51C, apex Greyed-Green 195D.

Peduncle:

*Length*.—Average range 18 to 25 cm.

*Width*.—Approximately 0.7 cm.

*Strength*.—Moderately strong.

*Texture*.—Glabrous.

*Color*.—Lower section near Greyed-Green 195C, upper section flushed Greyed-Red 182C.

Pedicels:

*Length*.—Approxiinately 1.0 cm.

*Width*.—Approximately 0.2 cm.

*Strength*.—Moderately strong and flexible.

*Texture*.—Glabrous.

*Color*.—Greyed-Orange N170C.

Fragrance: None detected.

REPRODUCTIVE ORGANS

Stamens: (Androecium).

*Number*.—Average 10.

*Filament length*.—Approximately 0.8 cm.

*Filament color*.—Near RHS Yellow 12B.

*Anther length*.—0.1 cm.

*Anther color*.—Near RHS Yellow 12A.

*Anther shape*.—Oblong.

*Pollen color*.—Near RHS Yellow 10D.

*Pollen quantity*.—Scant.

Pistil: (Gynoecium).

*Number*.—Average 5.

*Length*.—Approximately 1.2 cm.

*Style color*.—Near Green 143B.

*Stigma*.—Shape: Linear. Color: Near Green 143A. Ovary Color: Near RHS Yellow 6D.

OTHER CHARACTERISTICS

Fruits and seeds: Scant to moderate quantity of seeds. Seeds dust like, colored brown near RHS N200.

Temperature tolerance: Tolerates temperatures from approximately −2° C. to at least 38° C.

Disease/pest resistance: Resistance to *Fusarium echeveriae*. Neither resistance nor susceptibility to normal pests of *Echeveria* observed.

Drought tolerance: Tolerates at least 3 weeks of high temperatures without supplemental water, showing no serious damage to plant.

What is claimed is:

1. A new and distinct cultivar of *Echeveria* plant named 'ARCTIC ICE' as herein illustrated and described.

* * * * *